United States Patent [19]

Conn

[11] 4,173,139
[45] Nov. 6, 1979

[54] ULTRASONIC REFERENCE STANDARD AND THE METHODS OF CONSTRUCTION AND USE THEREOF

[75] Inventor: Don L. Conn, Middletown, Ohio

[73] Assignee: Armco Steel Corporation, Middletown, Ohio

[21] Appl. No.: 898,666

[22] Filed: Apr. 21, 1978

[51] Int. Cl.² .............................................. G01N 29/04
[52] U.S. Cl. ................................................... 73/1 DV
[58] Field of Search ...................... 73/1 DV, 597, 617; D19/96, 97

[56] References Cited

U.S. PATENT DOCUMENTS

| D. 149,117 | 3/1948 | Funfrock | D19/97 |
|---|---|---|---|
| D. 221,601 | 8/1971 | Markarian | D19/97 |
| 2,467,301 | 4/1949 | Firestone | 73/617 |
| 3,169,393 | 2/1965 | Stebbins | 73/611 |
| 3,754,472 | 8/1973 | Dory | 73/617 |

OTHER PUBLICATIONS

Paton, "Proceedings of the ARPA/AFML Review of Quantitative NDE", 7/17/75, pp. 89-105.
Tittmann et al., "A Technique for Studies of Ductile Fracture in Metals Containing Voids or Inclusions", 2/24/76, pp. 320-323, vol. 7A.
Art-Vue, Inc., Gifts & Decor Access, p. 217.

Primary Examiner—Anthony V. Ciarlante
Attorney, Agent, or Firm—Frost & Jacobs

[57] ABSTRACT

A reference standard for calibrating ultrasonic flaw detection test equipment and the like. The standard comprises a substantially solid body having at least one surface adapted to be engaged by the test equipment and a void of known dimensions located within the body at a known distance from the test equipment engaging surface. The standard may be constructed of two or more substantially solid bodies, at least one of which contains an aperture of known dimensions, and at least one of which is of known length and contains a surface adapted to be engaged by the test equipment, the bodies being diffusion bonded together to substantially eliminate the bond line such that the aperture forms a void of known dimensions within the substantially solid body at a known distance from the equipment engaging surface. In one embodiment, test equipment may be dynamically calibrated by rotating the standard about its longitudinal axis to produce a dynamic calibrated signal. The void formed within the standard by the aperture may be filled with an inclusion representing material to realistically modify the ultrasonic reflectance and attenuation characteristics.

11 Claims, 16 Drawing Figures

ULTRASONIC REFERENCE STANDARD AND THE METHODS OF CONSTRUCTION AND USE THEREOF

BACKGROUND OF THE INVENTION

1. Field of the Invention

The present invention relates generally to standards for calibrating ultrasonic test equipment, and more particularly to a substantially solid reference standard having a void of known dimensions contained therein at a known distance from the end of the standard adapted to be engaged by the test equipment.

2. Description of the Prior Art

Ultrasonic test equipment for detecting flaws in metallic and non-metallic parts is widely used for nondestructive inspection of raw and finished materials. Pulsed ultrasonic sound waves generated by a transmitting transducer such as piezoelectric crystal are transmitted into the parts to be inspected, such that any internal defect or flaw, such as a crack, void or other discontinuity in the part, will cause a portion of the sound waves impinging on the defect to be reflected back toward the same or a different receiving transducer, which converts the reflected wave into an electrical signal. The time interval between the transmission of the sound pulses to the body and the reception of the reflected sound pulse from the defect is a measure of the location of the defect. In addition, the magnitude of the reflected pulse is a measure of the size of the defect as viewed in the direction of travel of the sound waves.

Historically, ultrasonic test equipment of this type has been calibrated by using block-like reference standards in which a plurality of holes of various depths and diameters are drilled. However, such standards have not proven entirely satisfactory due to the difficulty in maintaining parallelism between the bottom surface of the hole and the transducer-abutting surface of the standard reference, as well as the surface finish at the bottom surface of the hole, both of which contribute to variances in the reflected sound waves and hence an unreliable reference calibration signal. For example, it has been found that the "flat bottomed" hole in prior art standards is not truly flat, but contains sufficient curvature and irregularities to introduce significant calibration errors in ultrasonic waves reflected from its surface. In addition, since such holes may be of a very small diameter, the drill bit used to produce the hole may "walk", resulting in holes of nonlinear axis or varying cross sectional area. The interior surfaces of such holes produce erratic reflection of ultrasonic energy which reduces calibration accuracy. Furthermore, this structure does not accurately duplicate the real-life flaw environment, wherein a void or other discontinuity is located completely within a surrounding solid body. In addition, prior art reference standards have not been able to simulate foreign particulate inclusions and the like located within the void. Finally, known reference standards used with test equipment to dynamically test rotating bar stock have heretofore been incapable of providing a dynamic calibration signal.

SUMMARY OF THE INVENTION

The present invention overcomes the deficiencies of the prior art devices by providing an ultrasonic reference standard with predetermined reflectance characteristics for improved calibration accuracy. In general, the reference standard comprises a substantially solid body having at least one surface adapted to be engaged by ultrasonic test equipment, such as an ultrasonic transducer, and a void of known dimensions located within the body at a known distance from the test equipment engaging surface. The reflecting surface of the void, as well as its dimensions and distance from the test equipment abutting surface which determines the ultrasonic sound travel distance, are carefully controlled so that the percentage of energy reflected from the void is accurately known and more realistically emulates actual test conditions.

The void thus formed within the substantially solid body may be filled with an inclusion representing material likely to be found in the material under test. The inclusion representing material modifies the ultrasonic wave transmission to realistically provide return signals closely resembling those to be found under actual test conditions.

In one embodiment, the reference standard comprises a thin plate-like wafer of known thickness containing at least one aperture of known dimensions bonded between a pair of substantially solid end pieces, such that the wafer aperture forms a void of predetermined dimensions within the standard. At least one of the end pieces is of known length and has at least on surface adapted to be engaged by the test equipment, such that the void is positioned within the standard at a known distance from the test equipment abutting surface. It is preferred that the end pieces and wafer be joined by diffusion bonding, which substantially eliminates the bond line between the members, thereby reducing spurious reflections within the standard. In addition, the wafer aperture may be filled with an inclusion representing material prior to assembly to alter the reflection characteristics of the standard in a realistic fashion.

The void may also be positioned within the test standard at various distances from one or more test equipment abutting surfaces, thereby permitting one test standard to serve as a reference for several travel distances. In fact, by properly positioning the void, a linear succession of travel distances may be provided from each of several test equipment abutting surfaces for verifying the distance/amplitude correction curve of the equipment.

In order to insure that the reflecting surface of the void is parallel to the test equipment abutting surface, thereby insuring predictable reflection of ultrasonic energy introduced into the standard, the surface of the end piece adjacent the void may be finished to any degree desired, thereby eliminating inaccuracies produced by prior art reference standards with unpredictable reflecting surface characteristics. Also since the depth of the aperture forming the void is small in comparison to its width, the linearity of the aperture axis can be maintained to a degree heretofore impossible with prior art reference standards.

In another embodiment of the present invention, a reference standard comprising a void contained within a substantially solid body rotatable about its longitudinal axis finds particular utility in dynamic test configurations used to test round bar stock and the like. Such prior art test configurations have been unable to dynamically calibrate the test equipment by continuously rotating the test standard, thereby simulating actual test conditions. However, the reference standard and test method of the present invention permits dynamic calibration of such test equipment while maintaining a high degree of accuracy and repeatability.

In a further embodiment of the invention, the test standard is formed by bonding together, preferably by diffusion bonding, two substantially solid end pieces, at least one of which contains an aperture of known dimensions, and at least one of which is of known length and contains a surface adapted to be engaged by the test equipment. In this embodiment, the surface of the end piece adjacent the void may be finished to a degree desired to produce an accurate energy-reflecting surface. The aperture may extend entirely through the end piece, or may consist of a flat-bottomed hole as in prior art designs. In this configuration, it is the finished surface of the adjoining end piece, rather than the surface of the flat-bottomed hole forming the aperture which reflects ultrasonic energy introduced at the test equipment abutting surface of the standard.

In general, the various embodiments of the reference standard of the present invention are utilized in the same manner as prior art reference standards. However, inasmuch as the dimensions and surface finishes of the void can be controlled to a degree heretofore impossible, the accuracy of the reference calibration signal is greatly improved. In addition, the inclusion-representing material located within the void modifies the reflected ultrasonic signal in a realistic manner to also improve the accuracy of the reference standard.

DESCRIPTION OF THE PREFERRED EMBODIMENTS

Figure 1:
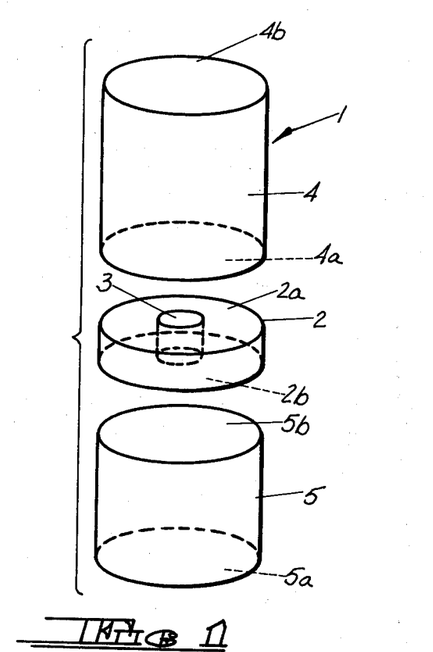
FIG. 1 is an exploded perspective view of one embodiment of the reference standard of the present invention prior to bonding.

FIG. 1 illustrates an exploded perspective view of one embodiment of the ultrasonic reference standard prior to assembly and bonding. The standard, shown generally at 1, comprises a thin cylindrical plate-like wafer 2 of known thickness containing a round aperture 3 therethrough of known dimensions sandwiched between first and second substantially solid cylindrical end pieces 4 and 5. As shown in FIG. 1, the upper surface 2a of wafer 2 and the lower surface 4a of end piece 4 are provided with a smooth surface to produce a relatively close fit when wafer 2 and end piece 4 are mated together. Lower surface 2b of wafer 2 and upper surface 5b of end piece 5 are similarily finished to provide a corresponding close fit when end piece 5 is mated to wafer 2. This insures that the planar boundaries formed by the surfaces will substantially disappear when the members are diffusion bonded together, as will be explained hereinafter. While for purposes of an exemplary showing the reference standard is illustrated and described in terms of cylinder-like members as might be formed from round bar stock, it will be understood that other shapes may be utilized, such as square, hexagonal, or octagonal. It will be further understood that the specific shape of the void formed within the standard may be altered as required for particular applications or reference standard shapes.

Upper surface 4b of end piece 4 is finished so as to be engaged by the transducer or other input device of the test equipment. In some test configurations, the transducer may not directly contact surface 4b, but may be acoustically coupled thereto by a suitable coupling fluid or the like. In any event, it is preferred that surface 4b be substantially parallel to surface 4a of end piece 4 when reference standard 1 is assembled. Maximum energy transference is attained by providing a smooth surface for surface 4a, which in association with aperture 3 form the reflecting surface of the void positioned within the test standard. Inasmuch as the void formed by aperture 3 when the members are assembled is of known dimensions, and is located a known distance from test equipment abutting surface 4b, the calibration accuracy of the test pattern is carefully controlled. Furthermore, since reflecting surface 4a is planar and parallel to surface 4b by which ultrasonic energy is introduced into the test standard, predictable and repeatable energy reflection is obtained. It will further be observed that inasmuch as the length of aperture 3 forming the void is small in comparison to its width, the axis and side walls of the aperture can be maintained substantially perpendicular to surface 4b, thereby insuring that reflected energy is not lost thru spurious internal reflections.

In general, it is contemplated that the test standard will be constructed of the same material as that to be tested, in order to insure matching sound transmission velocities and attenuation properties. In addition, in order to provide more realistic calibraton effectiveness, aperture 3 may be filled prior to assembly with an inclusion-representing material likely to be found within the voids in the part to be tested. For example, in the testing of steel parts, likely inclusion materials include iron oxide, manganese silicate and manganese sulfide. Such additives may be compacted, if desired, to more accurately simulate the rolled-in inclusions found during inspection of a product. Of course, the specific material used will depend upon the properties and characteristics of the part tested.

Figure 2:
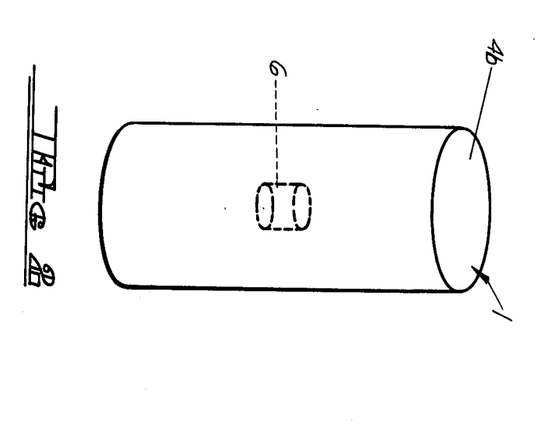
FIG. 2 is a perspective view of the reference standard of FIG. 1 after assembly and bonding.

The reference standard is assembled by sandwiching wafer 2 between end pieces 4 and 5, with or without the inclusion representing materials, as required, and induction heating the entire assembly at such a temperature that the mating surfaces of wafer 2 and end pieces 4 and 5 will bond by diffusion, thus substantially eliminating the surface boundaries between these members to produce a unitary structure as shown in FIG. 2, as is well understood in the art. While it is preferred that materials capable of being diffusion bonded, whether similar or dissimilar, be used in the construction of the reference standard, it will be understood that any material may be utilized capable of being joined to produce a bond line which provides minimal impedance to ultrasonic waves introduced into the standard. Furthermore, while diffusion bonding is the preferred method of joining the members making up the test standard, any method may be used which produces reflections from the bond interface which do not interfere with the reflections produced by the void. Thus, as depicted in FIG. 2, there results a substantially solid body having a void 6, of know dimensions and controlled reflectance characteristics contained therein at a known distance from the equipment engaging surface 4b.

To provide a more versatile test standard, lower surface 5a of end piece 5 may also be finished to be engaged by the test equipment so that sound waves may be injected into the standard from either end. With this arrangement it will be understood that surface 5b should also be provided with the required finish and flatness to insure optimum reflectance characteristics. Furthermore, by adjusting the relative lenghts of end pieces 4 and 5, the void 6 formed by aperture 3 and wafer 2 may be positioned at different travel distances from either test equipment abutting surface of the standard, thereby enabling one standard to serve the function of two. Such a construction permits more than one calibraton point to be obtained without the necessity of changing the position of the ultrasonic transducer associated with the test equipment.

Figures 3, 4:
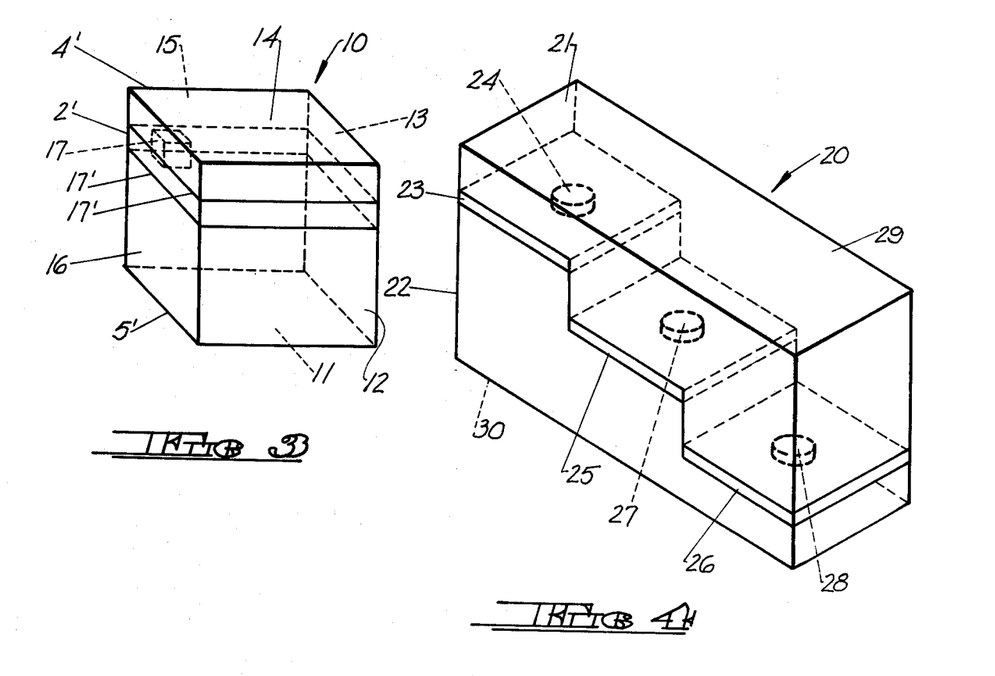
FIG. 3 is a perspective view of a reference standard containing an eccentrically located interior void.
FIG. 4 is a perspective view of a reference standard containing voids positioned at multiple travel distances.

FIG. 3 illustrates a second embodiment of the reference standard of the present invention, shown generally at 10, comprising a cube-like body containing multiple test equipment abutting surfaces 11–16, and a cube-like void 17 eccentrically positioned within the interior of the standard 10. The planar surfaces of void 17 are substantially parallel to their corresponding surfaces 11–16 of the standard 10 to insure optimum ultrasonic energy reflectance. Utilizing the construction of FIG. 3, void 17 may be positioned as to provide a different travel distance from each of the test equipment abutting surfaces 11–16, thereby providing six different calibration points for the flaw detection apparatus. By properly positioning void 17, a linear succession of travel distances may be provided from each of the surfaces 11–16 for checking the travel distance reflected wave amplitude correction curve for the test equipment. While the embodiment of FIG. 3 has been described and illustrated in connection with a cube having six surfaces, it will be understood that solid objects having a greater, or fewer number of surfaces may be provided in association with an eccentrically located void of the proper shape to produce any desired number of different travel distances and consequently any desired number of calibration points. This embodiment may be constructed in accordance with the procedure described hereinabove, by bonding a thin plate-like wafer 2' containing an aperture of the proper shape to form void 17 between a pair of substantially solid end pieces 4' and 5'. Where the members are joined by diffusion bonding, bond lines 17' will substantially disappear. As in the embodiment of FIG. 1–FIG. 2, the void 17 may be filled with any suitable inclusion representing material.

FIG. 4 illustrates a further refinement of the reference standard of the present invention, shown generally at 20, containing voids positioned at multiple travel distances. This type of construction finds particular utility in calibrating equipment used with square bar stock. Reference standard 20 comprises a pair of stair-step-shaped end pieces 21 and 22 which mate along their stepped surfaces to form a rectangular parallelepiped. As in previous embodiments, a thin plate-like wafer such as that shown at 23 containing an aperture 24 therein is sandwiched between end pieces 21 and 22 at each stair-step level. The thickness of wafer 23 and the dimensions of aperture 24 may be adjusted as described hereinabove. Additional wafers such as those shown at 25 and 26, containing apertures 27 and 28, respectively, may also be provided on successive stairstep levels so as to provide a plurality of voids within reference standard 20 when the wafers are sandwiched between the end pieces. The height of each stairstep may be dimensioned so as to position each void a predetermined distance from test equipment abutting surface 29. If desired, surface 30 opposite surface 29 may also serve as an equipment abutting surface so that reference standard 20 can be used to provide as many as six different travel distances. As described hereinabove, inclusion-representing material may be provided in some or all of the voids, and the wafers may be joined to the end pieces by diffusion bonding or the like. In this embodiment, the reflecting surfaces associated with apertures 24, 27 and 29 will be finished as described hereinabove. If diffusion bonding is used to join the members forming standard 20, the bond lines will essentially disappear. Although the embodiment of FIG. 4 has been described and illustrated as containing three voids, it will be understood that the reference standard may be caused to contain as many voids as required by providing the requisite number of stair-step levels, wafers and apertures.

Figure 5:
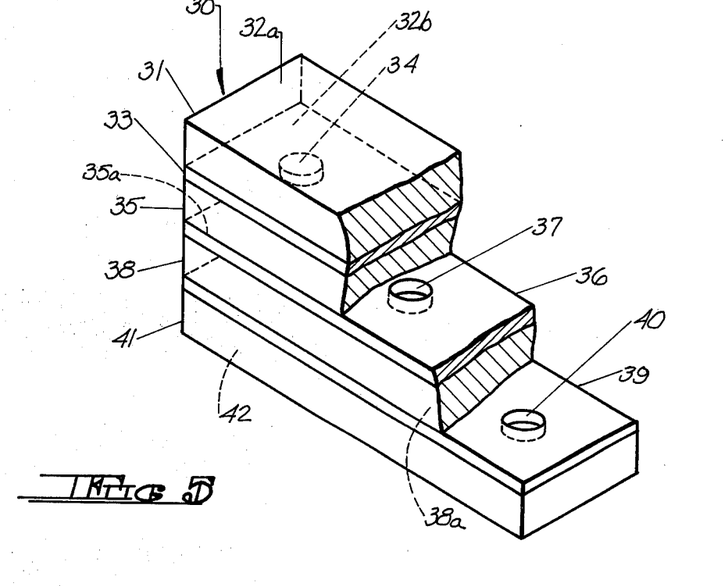
FIG. 5 is a fragmentary perspective view of an alternate construction for the reference standard of FIG. 4.

FIG. 5 illustrates an alternate construction to produce a reference standard, shown generally at 30, containing a plurality of voids with different travel distances similar in operation to that described hereinbefore in connection with the embodiment of FIG. 4. Reference standard 30 comprises a laminated structure containing alternating solid and aperture containing plates. As shown in FIG. 5, the outer end piece 31 contains an upper surface 32a adapted to engage the test equipment, and a lower surface 32b having the required reflectance characteristics. A thin plate-like wafer 33 is bonded by means of diffusion or the like to the surface 32b of end piece 31. Wafer 33 contains an aperture 34 of known dimensions therein, which may be filled with an inclusion-representing material as described hereinbefore. Wafer 33 is in turn bonded to a substantially solid plate-like member 35. The finished lower surface 35a of member 35 is bonded to the upper surface of a second plate-like wafer 36. Wafer 36 also contains an aperture 37 of known dimensions which may also be filld with an inclusion-representing material if desired. The opposite surface of wafer 36 is bonded to a second substantially solid member 138. A third plate-like wafer 39 containing an aperture of known dimensions 40 is sandwiched between member 38 and a substantially solid end piece 41, the lower surface 38a of end piece 38 being substantially parallel to test equipment abutting surface 32. Aperture 40 may also be filled with an inclusion-representing material, if required. As shown in FIG. 5, apertures 34, 37 and 39 are staggered so that no two apertures simultaneously receive and reflect ultrasonic energy introduced at surface 32. The thicknesses of solid members 31, 35, 38 and 41, and the thicknesses of wafers 33, 36 and 39 may be dimensioned so as to position voids 34, 37 and 39 at predetermined distances from test equipment abutting surface 32. It will be understood that the outer surface 42 of end piece 41 may also be adapted to be engaged by the test equipment, and the opposite surfaces of solid members 35, 38 and 41 may be so finished that ultrasonic energy may be introduced at either surfaces 32 or 42 so as to provide six possible different travel distances as in the embodiment of FIG. 4.

Figure 6:
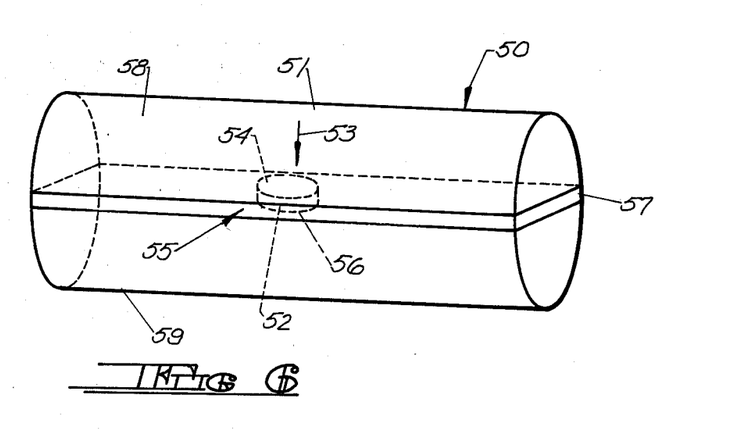
FIG. 6 is a perspective view of a reference standard for use with dynamic calibration test configurations.

FIG. 6–FIG. 8 illustrate an improved reference standard, shown generallya at 50, which finds particular utility in dynamic test configurations used to test round bar stock and the like. In such test set-ups, the round bar to be tested is submerged in a water tank and rotatably supported by cradle rolls. The submerged bar is then rotated about its longitudinal axis and an ultrasonic transducer moved axially along the bar so as to introduce ultrasonic sound waves of known characteristics into the bar being tested. The resulting ultrasonic reflections received at the transducer caused by internal defects or flaws may be observed and interpreted by means of an appropriate display device. In some situations, a transmitting and receiving transducer associated with the test equipment are arranged either coaxially or radially for inspection of the test piece using compression waves; in other situations, the transmitting and receiving transducers are angularly disposed to the test piece to inspect using shear waves. In such test configuratons, the water or other fluid in which the bar is submerged serves to couple the ultrasonic energy from the transducer to the bar under test, thereby eliminating direct physical contact between the transducer and bar.

FIG. 7A–7D illustrate a prior art reference standard bar used to calibrate such dynamic test set-ups. In this arrangement, a substantially cylindrical bar 60, shown in end view, containing a flat bottomed hole 61 extending radially outwardly from the longitudinal axis of bar 60 is submerged in a suitable coupling fluid (not shown) proximate an ultrasonic transducer 62. Bar 60 is so mounted that it may be rotated in the direction shown by arrow 63 about its longitudinal axis.

Figure 7A:
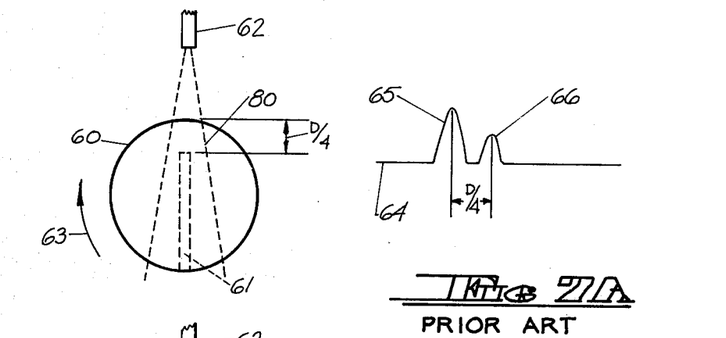
FIG. 7A-FIG. 7D are schematic representations of calibration waveforms produced by a prior art reference standard used in a dynamic calibration test configuration.

In many test configurations, it is desirable to have a travel distance within the test standard D/4, D/2, or 3D/4 according to some MIL test specifications, where D is the diameter of the reference standard. FIG. 7A illustrates such a conventional test standard utilizing a flat-bottomed hole 61 dimensioned such that the bottom surface of hole 61 lies at a distance 3D/4 from the upper surface of test standard 60 when the opening of hole 61 is removed from ultrasonic transducer 62 as illustrated in FIG. 7A. In this position, the ultrasonic reflections from the hole within bar 60 will produce the characteristic wave form shown at 64, having a first pulse 65 representing incident ultrasonic energy introduced into bar 60 followed by a smaller pulse 66 representing reflective ultrasonic energy from flat bottom hole 61. Pulses 65 and 66 will be displaced by an interval corresponding to the distance 3D/4. The amplitude of pulse 66 will depend partly upon the surface area of the botom hole 61, which for prior art "flat-bottomed" holes cannot be accurately calibrated. A further problem occurs when bar 60 has rotated such that the opening to hole 61 is adjacaent transducer 62, as will be described in connection with FIG. 7B–FIG. 7D hereinbelow. Finally, it will be observed that the type of hole 61 illustrated in the prior art reference standard of FIG. 7A can only produce a calibration signal for a travel distance of 3D/4. This necessitates using several different reference standards to provide a plurality of different travel distances.

Figure 7B:
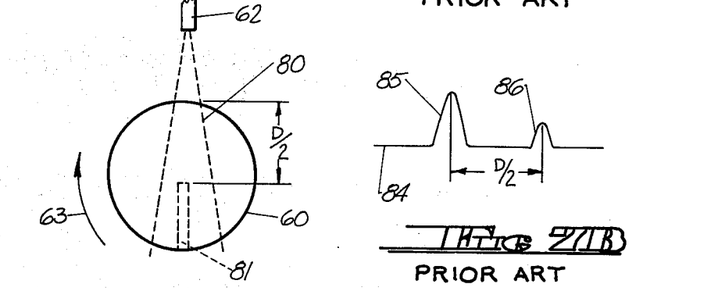
Figure 7C:
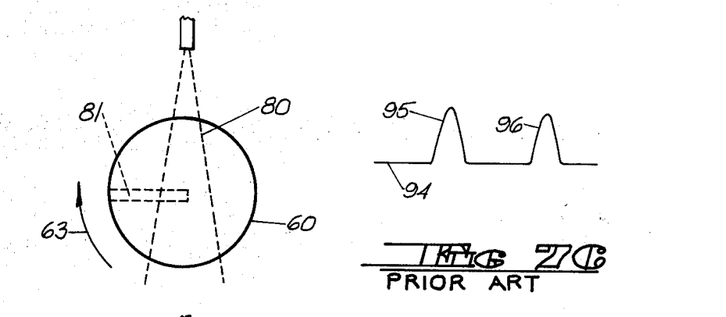
Figure 7D:
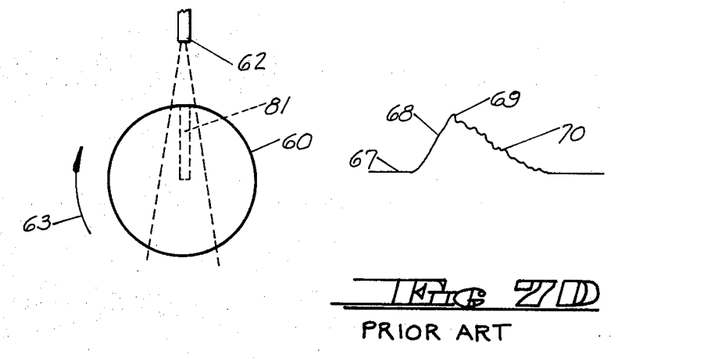

FIG. 7B–FIG. 7D illustrates a prior art test standard containing flat-bottomed hole 81 dimensioned to provide a travel distance of D/2. When prior art test standard 60 is in the position shown in FIG. 7B with the opening to hole 61 removed from transducer 62, ultrasonic energy 80 introduced into bar 60 by transducer 62 will be, in part, reflected from the bottom surface of hole 81, to produce the typical pulse pattern shown at 84, having a first pulse 85 representing incident ultrasonic energy into bar 60, followed by a smaller pulse 86 representing reflected ultrasonic energy from flat-bottom hole 81. The relative spacing between pulse 85 and pulse 86 will correspond to the travel distance D/2. It will be observed that irregularities in the bottom surface of hole 81, or errors introduced in the drilling of hole 81, such as drill "walk", etc., will appear as calibration inaccuracies in the reflected signal.

When the test bar has been rotated 90° to the position shown in FIG. 7C, such that the axis of hole 81 lies approximately transverse to the incident ultrasonic energy 80, the characteristic wave pattern 94 will be produced, having a first peak 95 representing incident ultrasonic energy introduced into bar 60, followed by another pulse 96 representing energy reflected from the side walls of flat-bottom hole 81. The amount of incident energy 80 impinging on the side walls of hole 81, when bar 60 is in this position, produces a spurious signal which can interfere with the calibration process. Thus the pulse height of pulse 96 cannot be relied upon to serve as a calibration reference.

Finally, when bar 60 has rotated to the position shown in FIG. 7D such that the opening to hole 81 is adjacent transducer 62, the characteristic waveform will appear as shown at 67. Waveform 67 comprises a smooth rising leading edge 68 representing the leading edge of the ultrasonic energy pulse introduced into bar 60, followed by a jagged peak 69 and jagged trailing edge 70 representing multiple reflections from the side walls and opening of hole 61.

In the prior art test configuration described in FIG 7A–FIG. 7B, the reference standard is usually placed in a test cradle with the opening of hole 61 or 81, as the case may be, directed away from transducer 62. The test standard in then manipulated until a maximum reflected signal output is observed. There is no guarantee that the bottom surface of hole 61 or 81, as the case may be, is in fact positioned perpendicular to the incident ultrasonic energy 80. Such a maximum amplitude pulse reading for the reflected pulse could also occur as a result of unpredictable variations in the bottom surface of hole 61, such as flatness and alignment, which will adversely effect the reflective characteristics.

Reference standard 50 comprises a substantially solid bar-like cylinder 51 containing an emplaced void 52. Reference standard 50 may be constructed by diffusion bonding a thin plate-like wafer 57 containing an aperture 52 between a pair of substantially solid semi-cylinder like end piece 58 and 59, so that the completed structure is essentially cylindrical in cross section. Reference standard 50 may be made in any length compatible with the particular test set-up involved. In the embodiment of FIG. 6, void 52 is configured in the shape of a flat cylindrical disc so that a greater percentage of ultrasonic energy introduced into reference standard 50 in the direction of arrow 53 will be reflected from surface 54, than will be reflected from surface 56 of void 52 from energy introduced in the direction of arrow 55. However, it will be understood that void 52 may be constructed in any suitable shape to provide optimal reflectance characteristics, such that maximum energy is reflected when wafer 57 is perpendicular to incoming ultrasonic energy, and an insignificant amount of energy is reflected when standard 50 has rotated through 90° such that wafer 57 is parallel to incident radiation. For example, void 52 may be a rectangular aperture machined into wafer 57. In any event, it will be understood that the planar surfaces of end pieces 58 and 59 abutting wafer 57 will be finished to provide the desired reflectance characteristics. As described hereinabove, void 52 may also be filled with a suitable inclusion-representing material to produce more realistic calibration signals.

While for purposes of an exemplary showing, the test standard 50 has been illustrated in FIG. 6 as lying on the rotational axis of standard 50 at a distance D/2 from the outer surface of the standard, it will be understood that void 52 may be placed at any distance from the surface of standard 50 to produce a desired travel distance. For example, to conform to some MIL test specifications, travel distances of D/4 and 3D/4 may be required. Under these condition, void 52 would be positioned within standard 50 such that the distances from the surfaces of the standard to the surface of the void having the greatest surface area measures D/4 and 3D/4, respectively. Thus a single standard serves to produce two travel distances. It will further be understood that the test standard 50 may be constructed as described hereinbefore in connection with FIG. 1–FIG. 2 to produce a cylindrical void having an axis parallel to the rotational axis of standard 50. The operation of each of these embodiments will be described hereinbelow.

The operation of reference standard 50 in dynamic test set-ups and its advantages over the prior art of FIG. 7A–FIG. 7D are illustrated in FIG. 8A–FIG. 8D. Reference atandard 50 is generally submerged in a suitable coupling fluid (not shown) and rotated about its longitudinal axis at a known rate. Ultrasonic energy 80 introduced into the reference standard by transducer 62 is reflected from a void 52 positioned at a distance D/2 to produce the characteristic waveform shown at 120. In the position of reference standard 50 illustrated in FIG. 8A wherein surface 54 is exposed to incident energy from transducer 62, waveform 120 will exhibit a first peak 121 representing the incident energy and a second small peak 122 spaced therefrom a distance D/2 representing the energy reflected from void 52. The relative magnitude of peaks 121 and 122 will depend upon the extent of surface 54 exposed to energy from transducer 62, as well as the attenuation characteristics of the standard.

Figure 8A:
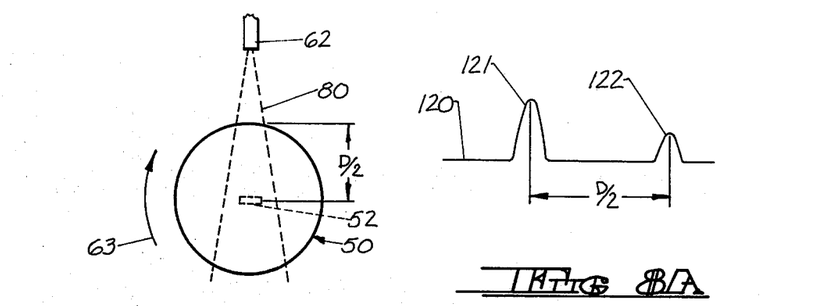
FIG. 8A-FIG. 8D are schematic representations of calibration waveforms produced by the reference standard of the present invention in a dynamic calibration test configuration.
Figure 8B:
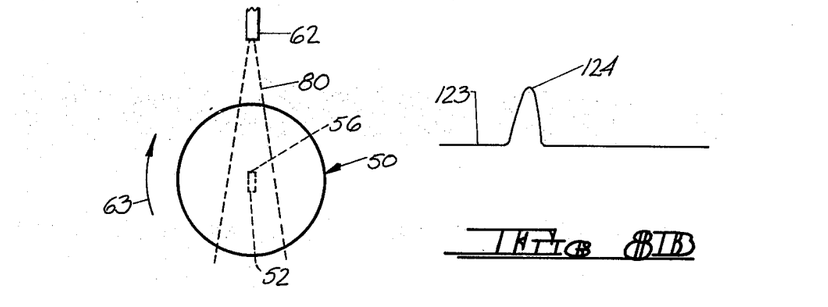

When reference standard 50 has rotated through an angular displacement of 90° as shown in FIG. 8B, such that narrow surface 56 of void 52 is exposed to transducer 62, characteristic waveform 123 will be produced wherein only the incident peak 124 is apparent. Since an insignificant amount of energy is reflected from the narrow surface 56, the reflected peak will be very small or non-existent. Thus is this test configuration, accurate and repeatable calibration wave forms are produced which may be interpreted to provide reliable calibration of the ultrasonic test equipment. If desired, standard 50 may be constructed in the manner of the embodiment of FIG. 1–FIG. 2 such that the cylindrical void would cause the amplitude of reflected peak 122 to remain relatively constant. In addition, transducer 62 may be caused to move in a direction parallel to the rotational axis of reference standard 50 so that the entire interior of the rotating bar under test may be scanned.

Figure 8C:
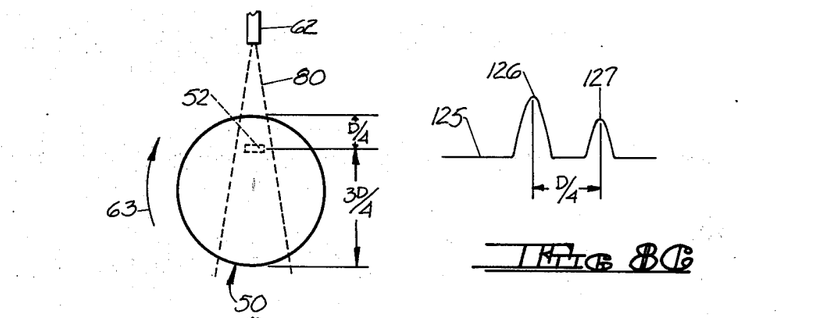
Figure 8D:
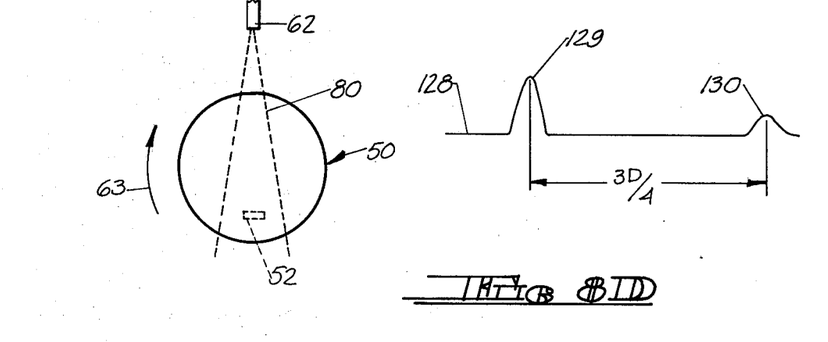

As described hereinabove void 52 may also be located at a distance D/4 from the outer surface of test standard 50, to produce travel distances of D/4 and 3D/4. The operation of this type of test standard in a dynamic test configuration is illustrated in FIG. 8B–FIG. 8D. When void 52 is positioned at a distance D/4 from the surface of standard 50 as shown in FIG. 8C, the characteristic waveform 125 will be produced, consisting of a first incident peak 126 and second smaller reflected peak 127 spaced therefrom a distance corresponding to D/4. It will be observed that when standard 50 has rotated in the direction of arrow 63 through an angular displacement of 90° (not shown), void 52 will lie outside beam 80, so that a waveform will be produced wimilar to that shown in FIG. 8B. Finally, when standard 50 has rotated through an angular displacement of 180° from its original position, such as that the void 52 is spaced a distance 3D/4 from the surface of standard 50, as shown in FIG. 8D, waveform 128 will be produced consisting of a first incident peak 129 and second smaller reflected peak 130 spaced therefrom a distance 3D/4.

Thus for any of the test configurations and test standard embodiments shown in FIG. 8A–FIG. 8D, test standard 50 may be continuously rotated to provide an accurate and repeatable dynamic calibration signal for any desired travel distance.

Figure 9:
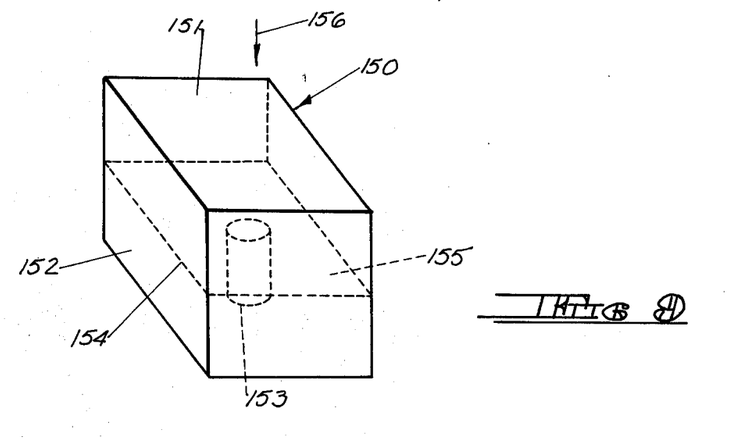
FIG. 9 is a perspective view of an alternative embodiment of the reference standard of the present invention.

A further refinement of the test standard of the present invention is illustrated in FIG. 9. The standard, shown generally at 150, comprises a pair of substantially solid end pieces 151 and 152 in the form of rectangular parallelepipeds which are joined along abutting surfaces to form a cube-like test block. One of the end pieces, such as 152, contains an aperture 153 of any shape therin, which may extend partially or completely through end piece 152. Surface 155 of test block 151 may be provided with any desired surface finish to provide the desired reflection characteristics. Ultrasonic energy introduced into test block 150 in the direction indicated by arrow 56 will thus be reflected from surface 155 adjacent aperture 153 to produce a predictable and repeatable reflected calibration signal. It will be understood that aperture 153 may be provided in any shape or size commeasurant with the particular test situation. In a preferred construction, when end pieces 151 and 152 are joined by diffusion bonding, bond line 154 will essentially disappear.

Figure 10:
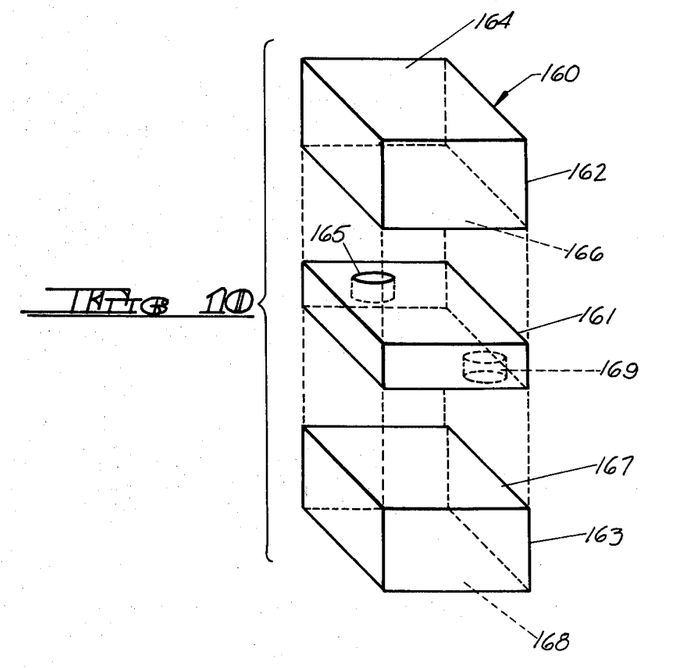
FIG. 10 is an exploded perspective view of a further embodiment of the reference standard of the present invention.

FIG. 10 illustrates a further embodiment of the test standard, shown generally at 160, of the present invention. A thin wafer-like plate 161 is sandwiched between substantially solid end pieces 162 and 163. End pieces 162 and 163 may be provided with a surface, such as that shown at 164 adapted to abut the test equipment to introduce incident ultrasonic energy into the test standard. Wafer 161 contains one or more apertures 165, of a shape and size determined to produce the necessary calibration parameters. It will be observed that apertures 165 may extend partly or completely through wafer 161, and in fact may take the form of flat-bottomed holes such as are known in the prior art. Surface 166 of end piece 164 adjoining wafer 161 is provided with a smooth planar surface to provide the necessary reflecting surface for energy introduced at test equipment abutting surface 164 of end piece 162, for use with aperture 165. Similarily, surface 167 of end piece 163 may be provided with a similar reflecting finish for energy introduced at test equipment abutting surface 168 of end piece 163 in connection with aperture 169. As in the embodiments described hereinabove, the members may be joined by diffusion bonding to substantially eliminate the bond lines.

It will be understood that as used herein, the surfaces of the various test standard embodiments adapted to be engaged and/or abutted by the test standard may refer to a surface adapted to directly contact a part of the test equipment, such as a transducer or the like, or may refer to a surface adapted to indirectly contact a part of the test equipment by means of a suitable ultrasonic coupler, such as a fluid.

It will be further understood that various changes in the details, materials, steps and arragements of parts, which have been illustrated and described in order to explain the nature of the invention, may be made by those skilled in the art within the principle and scope of the invention as expressed in the appended claims.

The embodiments of the invention in which an exclusive property or privilege is claimed are as follows:

1. A reference standard for calibrating ultrasonic flaw detecting test equipment and the like comprising a substantially solid body having at least two spaced surfaces adapted to be engaged and abutted by the test equipment for introducing ultrasonic energy into said body from either surface, and at least one void of known dimensions totally enclosed within said body at a known distance from said surface, said void having two spaced substantially planar surfaces configured to reflect substantially all of the ultrasonic energy impinging on said planar surfaces toward the test equipment, the volume of said void being substantially less than the volume of said body.

2. The reference standard according to claim 1 wherein said void is at least partially filled with an inclusion representing material.

3. The reference standard according to claim 1 wherein said void is positioned at different distances from some at least of said equipment abutting surfaces.

4. A reference standard for calibrating ultrasonic flaw detection test equipment and the like comprising first and second end members each having a substantially planar surface, and at least one thin plate-like wafer of known thickness having spaced substantially planar surfaces sandwiched between said end pieces, each of said planar surfaces of said wafer abutting a respective one of said planar surfaces of said first and second end pieces, said wafer including at least one aperture therethrough of known dimensions, each of said end pieces having its outermost end forming a surface configured to be engaged and abutted by the test equipment, said end pieces being of a known thickness such that said aperture forms a void of known dimensions at a known distance from said equipment abutting surfaces within said standard when said end pieces and said wafer are sandwiched together such that ultrasonic energy can be introduced at either of said test equipment abutting surfaces.

5. The reference standard according to claim 4 wherein one of said end pieces is of a thickness greater than said other end piece such that said void is positioned at a different distance from each of said surfaces.

6. The reference standard according to claim 4 wherein said aperture forming said void is at least partially filled with an inclusion representing material.

7. The reference standard according to claim 4 wherein said end pieces and said wafer are diffusion bonded to form a substantially unitary structure.

8. The reference standard according to claim 4 wherein said equipment abutting surfaces are positioned with respect to said void such that ultrasonic energy may be introduced into said standard in a direction parallel to the longitudinal axis of said standard.

9. The reference standard according to claim 4 wherein said equipment abutting surfaces are positioned with respect to said void such that ultrasonic energy may be introduced into said standard in a direction transverse to longitudinal axis of said standard.

10. The method for calibrating ultrasonic flaw detection test equipment and the like by introducing ultrasonic sound waves of known characteristics from the test equipment into a continuously rotating reference standard containing a void and receiving and interpreting waves reflected from said void comprising the steps of:
    (a) rotatably supporting a substantially cylindrical reference standard having a void of known dimensions totally enclosed within the standard at a known distance from the surface of the standard, said void having two spaced substantially planar surfaces configured to reflect substantially all of the ultrasonic sound waves impinging on said planar surfaces toward the test equipment;
    (b) continuously rotating the standard about its longitudinal axis;
    (c) introducing ultrasonic sound waves of known characteristics from said test equipment into said standard; and
    (d) receiving and interpreting waves reflected from said void to calibrate the test equipment.

11. The method according to claim 10 wherein said introducing step includes scanning said sound waves along the longitudinal axis of the standard.

* * * * *

UNITED STATES PATENT AND TRADEMARK OFFICE
CERTIFICATE OF CORRECTION

PATENT NO. : 4,173,139
DATED : November 6, 1979
INVENTOR(S) : Don L. Conn

It is certified that error appears in the above-identified patent and that said Letters Patent are hereby corrected as shown below:

On the title page, the assignee should be designated as Armco Inc.

Signed and Sealed this

Fifteenth Day of April 1980

[SEAL]

Attest:

SIDNEY A. DIAMOND

Attesting Officer

Commissioner of Patents and Trademarks